FIG. 3

US005874280A

United States Patent [19]
Keil
[11] Patent Number: 5,874,280
[45] Date of Patent: Feb. 23, 1999
[54] VECTOR VACCINES OF BOVINE HERPESVIRUS I
[75] Inventor: Günther Keil, Tübingen, Germany

[73] Assignee: Akzo Nobel N.V., Arnhem, Netherlands

[21] Appl. No.: 344,833

[22] Filed: Nov. 23, 1994

[30] Foreign Application Priority Data

Nov. 23, 1993 [EP] European Pat. Off. .............. 93203274

[51] Int. Cl.$^6$ .......................... C12N 7/01; A61K 39/245; C07H 21/04

[52] U.S. Cl. .................................... 435/235.1; 424/205.1; 424/229.1; 424/199.1; 536/23.72

[58] Field of Search ...................... 435/235.1; 424/205.1, 424/229.1, 199.1; 536/23.72

[56] References Cited

FOREIGN PATENT DOCUMENTS

| | | |
|---|---|---|
| A-0 547 446 | 6/1993 | European Pat. Off. . |
| WO92/21751 | 12/1992 | WIPO . |
| WO-A-93 02104 | 2/1993 | WIPO . |
| WO-A-94 00586 | 1/1994 | WIPO . |

OTHER PUBLICATIONS

J. Audonnet, *Protein Indentification Resource*, Ab. No. S35785, 22–Nov.–1993.

S.K. Tikoo et al., "Analysis of Bovine Herpesvirus 1 Glycoprotein gIV Truncations and Deletions Expressed by Recombinant Vaccinia Viruses," *Journal of Virology*, 67:4:2103–2109, Apr. 1993.

Leung–Tack et al. "The Complete DNA Sequence and the Genetic Organization of the Short Unique Region . . . " Virology 199, 409–421 (1994).

Fehler et al. "Glycoprotein IV of Bovine Herpesvirus 1—Expressing Cell Line Complements . . . " J Virol 66(2) Feb. 1992 pp. 831, 839.

Ramshaw et al. "Cytokine Expression by Recombinant Viruses . . . " TIBTECH vol. 10, Dec. 1992, pp. 424–426.

*Primary Examiner*—Ponnathapura Achutamurthy
*Assistant Examiner*—Phuong T. Bui
*Attorney, Agent, or Firm*—William M. Blackstone

[57] ABSTRACT

The present invention is concerned with a Bovine Herpesvirus I (BHV-I) mutant comprising a heterologous gene introduced into a section of the BHV-I genome. The invention also relates to a vector vaccine comprising such a BHV-I mutant which expresses a heterologous polypeptide derived from a bovine pathogen and induces an adequate immune response in an inoculated host against both FHV an the bovine pathogen. Furthermore, the invention relates to a method for obtaining a BHV-I mutant by self-selection.

8 Claims, 10 Drawing Sheets

EOVIV gIV-ORF

1.  EOVIV x Tth111I
          x Bal31
          x XbaI
          x Klenow gIV-ORF

2.  pEMBL19 x SmaI
            + gIV-ORF pEMBL19-gIV-ORF

3. pEMBL19-gIV-ORF x EcoRI pEMBL19-gIV-ORF

*: gIV-ORF pEMBL19-gIV-ORF

⇓
pEMBL19-gIV-ORF x HindIII
                    x XbaI
                    x Klenow
⇓ gIV-ORF pLA1-6 pLA1-6 x BamHI
      x EcoRI
      x Klenow
      + gIV-ORF

*. gIV-ORF
+: gIV-Promotor

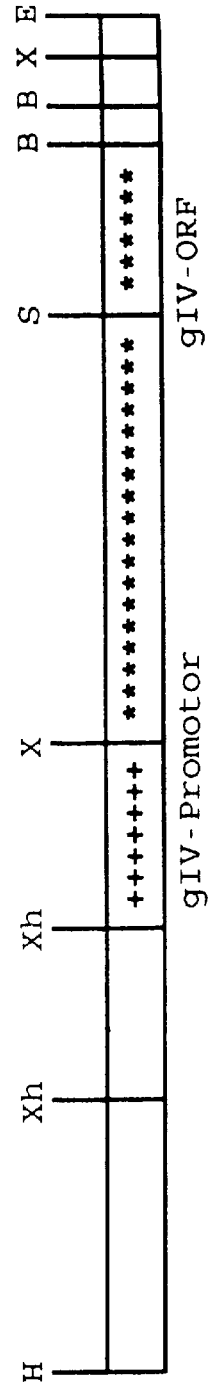
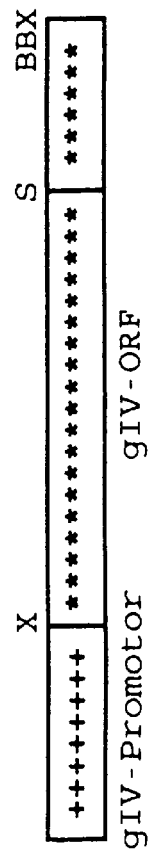
FIG. 6
FIG. 7

VECTOR VACCINES OF BOVINE HERPESVIRUS I

The present invention relates to a Bovine Herpesvirus I mutant comprising a mutation in a section of the BHV-genome, such a BHV-I mutant comprising a heterologous DNA sequence inserted in said section, a nucleic acid sequence comprising at least part of said section of the BHV-I genome, a recombinant DNA molecule comprising heterologous DNA flanked by DNA derived of said section, a host cell transfected with said nucleic acid sequence or recombinant DNA molecule, a host cell infected with a BHV-I mutant, a vaccine comprising a BHV-mutant, a method for the immunisation of animals against an infectious disease and a method for the preparation of a BHV-I mutant.

BACKGROUND OF THE INVENTION

The herpesviruses are a widespread family of large viruses containing double-stranded DNA, causing disease in mammals, birds, reptiles, fish and amphibians.

The double-stranded DNA codes for about 30–35 polypeptides, depending on the genus. The molecular weight of the DNA greatly varies between 120 kbp in Channel Cat Fish Herpesvirus to 230 kbp in Human Cytomegalovirus. The GC-content of the DNA varies even more; from 32% in Dog Herpesvirus to 72–73% in Bovine Herpesvirus.

The viral agent s causing Infectious Bovine Rhinotracheitis (IBR), Infectious Pustular Vulvovaginitis (IPV) and Infectious Balanoposthitis (IBP) belong to the Herpesviruses, more specifically to the sub-family Alphaherpesvirinae (Roizman, B. In Fields, B. N., Knipe, D. M. (ed.) Fundamental Virology. Ravens Press, New York: 841–847 (1991)).

They are all designated Bovine Herpesvirus I (Roizman et al.; Intervirology 16: 210–217 (1981)), and more recently Bovid Herpesvirus I (Ludwig, H. in B. Roizman (Ed.) The Herpesviruses. Plenum Press New York, vol. 2: 135–214 (1983)). In cross-neutralisation tests BHV-I isolates all exhibit only one serotype, regardless their origin from IBR or IPV/IBP cases (Gillespie et al.; Cornell Vet. 49: 288–297 (1959), McKercher et al.; Can. J. Comp. Med. 23: 320–328 (1959)). Restriction enzyme analysis of large numbers of different isolates has revealed differences in restriction site patterns, but no correlation exists between the patterns and the origin of the isolates. Therefore it is now generally accepted that the site of infection with BHV-I determines the effects of the disease, whereas the causative agent is in all cases the Bovine Herpesvirus I.

Transmission of Infectious Bovine Rhinotracheitis can occur for instance a) by animals that are acutely infected with or without showing clinical signs, and that are still shedding virus, and b) by animals that are latently infected and start shedding recurrent virus after stress.

Spread of IPV/IBP occurs e.g. by contaminated semen, natural service, the teaser bull, or by the herdsmen.

The most common manifestation of BHV-I infection is bovine rhinotracheitis which varies from a mild respiratory disease to a severe infection of the entire respiratory tract.

From an economical point of view, IBR is also the most dramatic manifestation of BHV-I infection.

Another relatively important form of BHV-I infection is the genital form, leading to pustular vulvovaginitis in cows and, comparatively, to infectious balanoposthitis in bulls.

Although seen less frequently, the virus is also associated with abortion, conjunctivitis and encephalitis. BHV-I is widely spread among cattle in all continents, but its host range is limited. Many wild species have been found seropositive, but distinct clinical signs have only been observed in cattle.

Although IBR and IPV have been known in Europe for more than a century, it appears that wild ruminants in Africa and in zoos are the true reservoir of the virus.

Morbidity rates in both IBR and IPV are usually 100% provided that the animals are in close contact (for IPV).

If morbidity is <100% then the animals are protected by antibodies. Fatalities are rare however, in the case of IBR and IPV. In young calves however, death as a result of BHV-I induced encephalitis is common. Next to this, several strains of BHV-I have shown to induce abortion. Due to secondary bacterial infections, pneumoniae and enteritis may occur (Bielefeld-Ohmann et al.; J. Infect. Diseases 151: 937–947 (1985))

Immunity against Herpesviruses is depending on at least two mechanisms: a) the induction of neutralising antibodies and complement-dependent lysis for the inactivation of free virus, and b) the induction of cytotoxic T-cells for the elimination of virus-infected cells.

At present, in general, cattle can be protected against infection by these pathogenic micro-organisms with live vaccines, inactivated vaccines and subunit vaccines.

However these types of vaccines may suffer from a number of drawbacks. The use of attenuated vaccines always carries the risk of inoculation of animals with inadequately attenuated pathogenic micro-organisms. In addition, the attenuated micro-organisms may revert to a virulent state resulting in disease of the inoculated animals and, consequently, spread of the pathogens to other animals. Moreover, a problem with combined live viral vaccines is the mutual influence of the antigenic components resulting in a decrease of potency of one or more of the components.

Inactivated vaccines are generally considered safe, but they generally induce only a low level of immunity, requiring repeated immunizations. Furthermore, the neutralisation inducing antigenic determinants of the pathogens may become altered by the inactivation treatment, decreasing the immunising potency of the vaccine. In addition, cellular immunity is to a lesser extend triggered by inactivated vaccines.

Subunit vaccines have the same drawbacks as inactivated vaccines, and additionally, their spectrum of protection is smaller since they contain less different antigenic determinants then the whole organism.

It is an object of the present invention to provide a safe live BHV-1 mutant which can be used not only for the preparation of a vaccine against Bovine Herpesvirus I, but also as a carrier of genetic information for antigenic determinants of other infectious diseases of cattle, which obviates any potential risk associated with the use of a live attenuated pathogen. Therefore the present invention is concerned with a vaccine, which stimulates both the cellular and humoral immune system in a potent way without the explicit need of an adjuvant and which offers the possibility of a multivalent vaccine without the risk of adverse mutual interference of different antigenic components.

SUMMARY OF THE INVENTION

The present invention provides a BHV-I mutant comprising a mutation in a section of a BHV-I genome, which is located adjacent to the 3' terminus of gIV and extending to the 3'-terminus of the adjacent ORF-1, i.e. the open reading frame encoding the polypeptide shown in SEQ ID NO: 2., and additionally comprising a poly-adenylation signal which is located between the 3' terminus of the gIV gene and the mutation.

A mutation is understood to be a change of the genetic information in the above-mentioned section in comparison to the genetic information present in this section of the genome of the parent BHV-I.

The mutation may be a nucleic acid substitution, deletion, insertion or inversion, or a combination thereof. In particular the mutation is an insertion, preferably of a heterologous gene.

Preferably, the mutation is incorporated into a gene encoding the polypeptide shown in SEQ ID NO: 2. (mentioned ORF-1 hereafter) or in the intergenic region between the gene encoding gIV and the gene encoding the polypeptide shown in SEQ ID NO: 2.

More in particular, the mutation is incorporated in the nucleic acid sequence shown in SEQ ID NO: 1.

BRIEF DESCRIPTION OF THE DRAWINGS

FIG. 3. Physical map of Eoviv.4930.

FIG. 6. Construction of pLA1-6-gIV-ORF.

FIG. 7. Construction of gIV-Prom-gIV-ORF.

DETAILED DESCRIPTION OF THE EMBODIMENTS

Figure 1A:
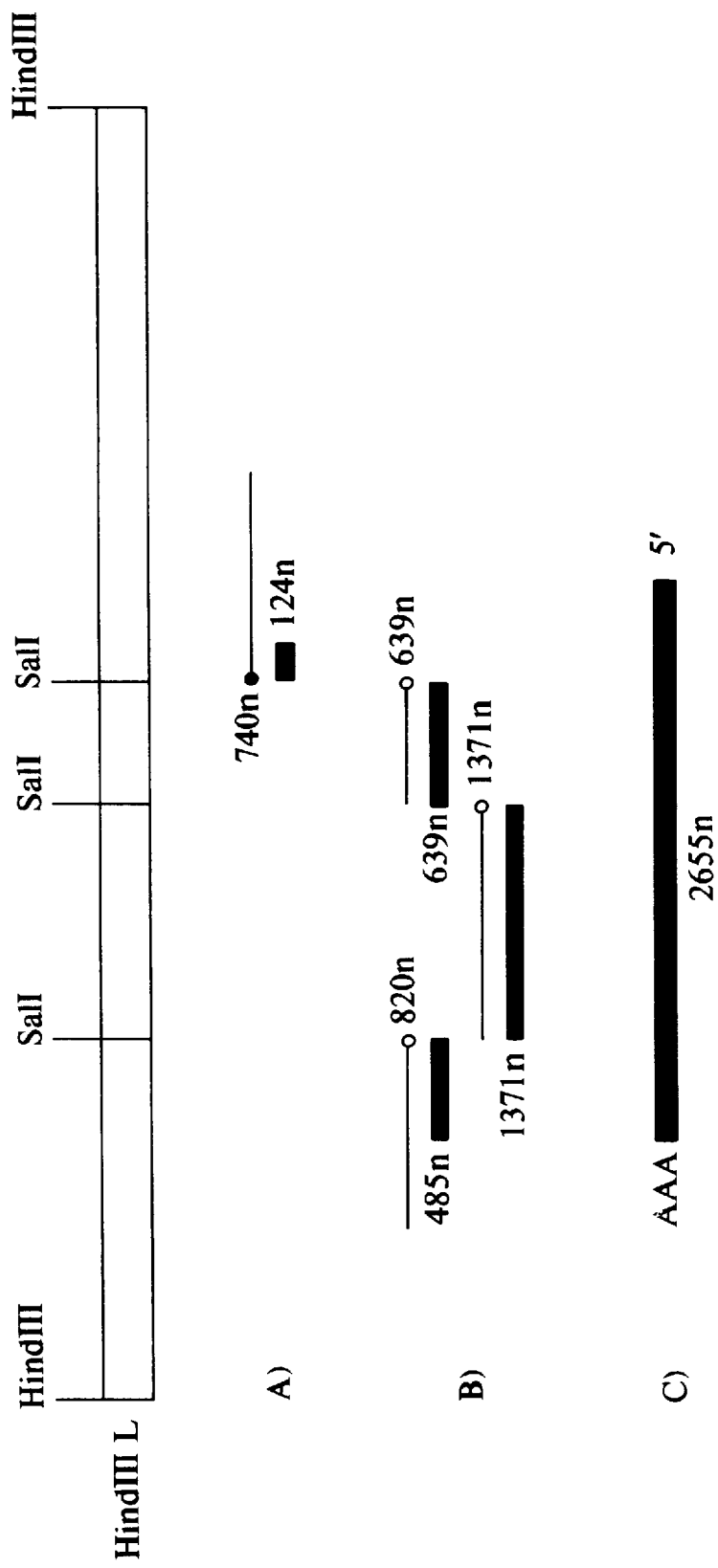
FIG. 1A. Schematic representation of nuclease S1 protection experiments.

The term "polypeptide" as used herein refers to a molecular chain of amino acids. "Polypeptide" does not refer to a specific length of the product. The polypeptide can if required be modified in vivo or in vitro, for example by glycosylation, amidation, carboxylation, myristylation or phosphorylation; thus inter alia, peptides, oligopeptides, and proteins, as well as modifications thereof, are included within the definition of polypeptide.

A poly-adenylation signal is a short sequence at the 3' terminus of RNA, which in most cases comprises a consensus sequence AAUAAA, is and encoded by the DNA-fragment from which the RNA was transcribed. Nascent RNA is cleaved at this signal by a specific endonuclease. Subsequently, a poly-A polymerase adds a long stretch (usually about 250) A-residues to the RNA beginning at the cleavage site.

No poly-adenylation signal has been found between the gIV gene and the gene coding for ORF-1. It has been shown by RNA-mapping, that the RNAs transcribed from the gIV gene and from the ORF-1 gene both use the poly-A signal downstream ORF-1, as follows: To determine the 5'- and 3' ends of the gIV mRNA, 5'- and 3'-end labeled DNA fragments from the genomic region spanning the gIV and ORF-1 gene were hybridised to RNA from BHV-1 infected cells and subsequently incubated with nuclease S1.

Protected fragments were separated on sequencing gels and visualised by autoradiography. Sizes were determined using end-labeled pBR322 HpaII DNA fragments. The results showed that the mRNA coding for gIV is initiated 25 nucleotides downstream the gIV promotor and terminates 45 nucleotides downstream the poly-A signal which follows ORF-1.

No 3' RNA-discontinuity was detected between the 5'-cap site and the 3'-poly-A signal determined above. Thus the mRNA coding for gIV terminates at the polyadenylation signal downstream ORF-1, i.e. the same signal where the mRNA for ORF-1 is polyadenylated (see Example 1 and FIGS. 1a, b).

In addition to this, it was experimentally shown, that it is impossible to rescue gIV-negative BHV-1 mutants lacking the poly-A signal downstream ORF-1, with a plasmid that contains the gIV coding sequence but no downstream poly-A signal.

The above mentioned results implicate that the RNA coding for the gIV gene product is relatively long. Therefore, modifications in the region between the gIV-gene and the poly-A signal may lead to a non-functional gIV RNA. Clearly, the deletion of the poly-A signal downstream ORF-1 would lead to a non-functional RNA. In order to circumvent this problem, in the present invention a poly-A signal was introduced between the gIV gene and the section indicated in the invention, in which mutations can be made. As a result, the gIV RNA is always provided with a poly-A signal.

Many poly-A signals have been sequenced, and they all share the consensus sequence mentioned above. The sequence of the surrounding nucleotides, the so-called context, may however highly differ from one gene to another. Thus heterologous polyadenylation signals can equally well be used downstream a certain gene, instead of the authentic poly-A signal. In the present invention, the poly-adenylation signal of the murine cytomegalovirus (MCMV) immediate early 2 (ie2) gene (Messerle et al.; J. Virol 65: 1638 ff. (1991)) was used as a heterologous poly-A signal. Other poly-A signals are e.g. the late poly-A signal of the Simian virus 40 (Schek et al., Mol. Cell. Biol. 12: 5386–5393 (1992)), a poly-A signal of HIV-1 (Valsamakis et al., Mol. Cell. Biol. 12: 3699–3705 (1992)) and the poly-A signal of the Bovine parathyriod hormone messenger (Weaver et al., Mol. Cell. Endocr. 28: 411–424 (1982)).

An intergenic region is a nucleic acid sequence that is generally found in between two coding regions. It may contain sequences that are involved in transcription initiation or termination, translation initiation, and the like.

It is possible that some amino acids in the polypeptide encoded by ORF-1 have been replaced by others while the polypeptide is not altered in its function. For instance, a polypeptide containing Asp at a certain site, and its variant containing Asn at the comparable site still have the same properties. This process in which an amino acid is replaced by an functionally analogous amino-acid is called functional displacement. In this case the variant proteins are called functional variants.

Another cause of variation is the phenomenon of degeneracy of the genetic code. Shortly, it means, that e.g. the amino acid glutamic acid is coded for by both GAT and GAA. This phenomenon holds for all amino acids, except Met and Trp. Thus, it is obvious, that the ORF-1 polypeptide given in the present invention can not only be coded for by the nucleotide sequence given in SEQ ID NO: 1 but also by a very large variety of other sequences, still all giving the same polypeptides.

Therefore, a variant BHV-1 sequence encoding a polypeptide that is functionally comparable to the ORF-1 polypeptide of the present invention can also be used in the invention.

Since there is little selective pressure on intergenic sequences, it is possible that variant BHV-1 strains can be found, that have an intergenic region between gIV-ORF and ORF-1 with a slightly different sequence. These variants do belong to the invention.

The prerequisite for a useful BHV-I mutant according to the present invention is, that the mutation is introduced into a permissive position or region of the genomic BHV-I sequence, i.e. a position or region which can be used for the incorporation of the mutation without disrupting essential functions of BHV-I such as those necessary for infection or replication.

Although the general genomic organisation of Bovine Herpesvirus with respect to e.g. length, location of Herpesvirus-characteristic repeats and unique regions has been determined (Ludwig, H. in: "The Herpesviruses", Vol. 2, B. Roizman ed., Plenum Press (1983)), knowledge of gene function, gene products and even the exact number of genes, is lacking. Only a few genes are well-studied: the Thymidine Kinase gene (Kit et al., U.S. Pat. Nos. 4,703,011 and 4,824,667) and the gX gene (gX is the nomenclature used for Pseudorabies-virus) (Kit et al., the Veterinary Record 127: 363–365 (1990) and European Patent EP 0.326.127). The gX-homolog gene gG from BHV-I has recently been localised and sequenced by Cochran et al. (PCT-application WO 93/02104). Also four major BHV-I glycoproteins gI, gII, gIII and gIV have been described in the literature (Fitzpatrick et al. J. of Virol. 62, 4239–4288 (1988), and three of the genes; gI (in fact the gI-homolog gene gE from BHV-I: gI is the PRV-nomenclature) (Whitbeck et al.; J. Virol. 62: 3319–3327 (1988)), (Rijsewijk (WO 92/21751)), gIII (Fitzpatrick et al.; Virology 173: 46–57 (1989)) and gIV (Tikoo et al., J. of Virol. 64: 5132–5142 (1990)) have been sequenced. Several of these genes have been found and localised on the basis of the structural or functional homology with their counterparts in Pseudorabies virus and Herpes simplex virus. This could of course only be done for 1) those genes that have sufficient sequence homology or for 2) those genes that code for polypeptides with significant homology to glycoproteins found in Herpes simplex virus and Pseudorabies virus (Fehler et al., J. of Virol., 66: 831–839 (1992)).

This is however only the case for few of the BHV-I genes, as can easily be concluded from e.g. the differences in GC-content or genome-length between various herpesviruses as mentioned above.

The section of the BHV-1 genome referred to in the present invention has been described partially in the literature. The gIV gene has been sequenced by Tikoo (Tikoo et al., J. of Virol. 64: 5132–5142 (1990)). Tikoo only sequenced the coding region, but he assumes the presence of a poly-A signal. This assumption however is not correct since no poly-A consensus-signal was found, as was mentioned above.

It has been surprisingly found now, that the gene coding for ORF-1 as described in the present invention allows mutations of the kind mentioned above, without disrupting information essential for the reproduction of the virus. There is however, as was also found, a certain proviso: expression of the essential gIV gene needs the presence of a poly-A signal at a reasonable distance of the gIV gene. Since gIV uses the poly-A signal of ORF-1, gIV has to be provided with a (homologous or heterologous) poly-A signal located between the gIV gene and the mutation, before mutations can be introduced in ORF-1.

Figure 2:
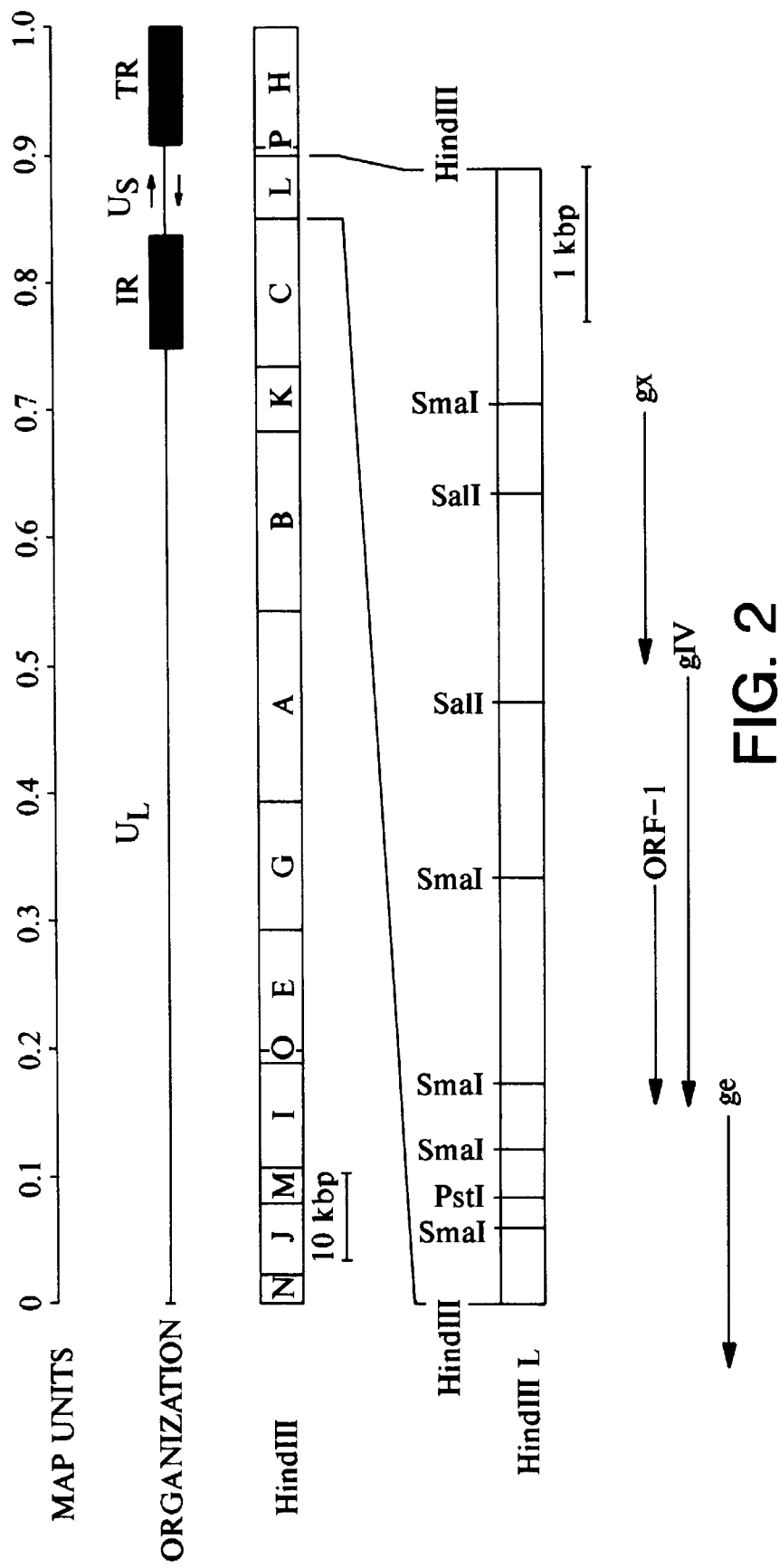
FIG. 2. Restriction map of the gIV/ORF-1 region. The arrows indicate the various RNAs.

The section of the BHV-I genome used to introduce one or more mutations in order to prepare a BHV-I mutant according to the invention is located within an about 4600 bp. fragment generated by partial digestion of the BHV-I DNA with the restriction enzyme SmaI. See FIG. 2.

The BHV-I mutant of the present invention thus comprises a mutation in a section of a BHV-I genome, which is located adjacent to the 3' terminus of gIV and extends to the 3' end of the adjacent ORF-1, and additionally comprises a polyadenylation signal which is located between the 3' terminus of the gIV gene and the mutation.

In particular, the BHV-mutant comprises a mutation in a section of a BHV-I genome that spans the DNA fragment of which the sequence is shown in SEQ ID NO: 1. This sequence represents the region comprising the open reading frame ORF-1 as represented by SEQ ID NO: 1 and the intergenic region between ORF-1 and gIV.

Also part of the invention is a BHV-I mutant comprising a heterologous DNA sequence in the above mentioned section.

A heterologous DNA sequence is a sequence that originates from a source, other than the parent BHV-I strain. It may be derived from the DNA of another organism or may be synthetically made. Also included is cDNA, made from heterologous RNA or heterologous single-stranded DNA.

The heterologous DNA sequence may be a random sequence or it may be a sequence that interferes with transcription or translation of ORF-1. Such sequences may be transcription termination signals or poly-adenylation sites but they may also contain translational stop-codons.

In a preferred form, the heterologous DNA sequence codes for a polypeptide.

The heterologous DNA sequence preferably contains promotor sequences such that expression is under control of these sequences. These sequences may be the promotor sequences that are found to be linked to the gene coding for the polypeptide, in its native form, or it may be other promotor sequences.

It is obvious to those skilled in the art that the choice of a promotor extends to any eukaryotic, prokaryotic, viral or synthetically prepared promotor capable of directing gene transcription in cells infected by the BHV-I mutant, e.g. promotors of the retroviral long terminal repeat (Gorman et al., Proc. Natl. Acad. Sci. U.S.A. 79, 6777–6781, 1982), the SV40 promotor (Mulligan and Berg, Science 209, 1422–1427, 1980) or the cytomegalovirus immediate early promotor (Schaffner et al., Cell 41, 521–530, 1985).

Sequences modulating expression such as e.g. enhancers are often found to play an essential role in transcription and transcription-levels, and are therefore also considered to be part of the transcription complex.

In a more preferred form, the heterologous DNA sequence encodes an antigen of a significant cattle-pathogen, which is able to elicit a protective immune response, whereby the antigen is expressed by the BHV-I mutant according to the invention upon replication in the host cell.

Preferably the antigen is chosen from the group of cattle pathogens, consisting of Bovine Rotavirus, Bovine Viral Diarrhoea virus, Parainfluenza type 3 virus, Bovine Paramyxovirus, Foot and Mouth Disease virus, Bovine Coronavirus, Bovine Respiratory Syncytial virus and Pasteurella haemolytica.

Furthermore, the heterologous DNA sequence may encode a cytokine. Several cytokines, e.g. interferons are known to play an important role as immune modulators. Thus it may be advantageous to include genetic information for this kind of molecule into said section.

It is obvious that a heterologous DNA sequence can be introduced at a certain site in said section, e.g. in a restriction site without deleting any nucleotides from the section. On the other hand, it is possible to exchange one or more nucleotides with heterologous DNA sequences of equal or different length.

Therefore, BHV-I mutants having a deletion in said section are also included in the invention, regardless the presence and size of a heterologous DNA sequence.

The technique of in vivo homologous recombination can be used to introduce a modified homologous nucleic acid sequence comprising a mutation in a section of the BHV-I genome as described above, or a heterologous nucleic acid sequence into the BHV-I genome.

Homologous recombination can be accomplished by first constructing a recombinant DNA molecule for recombination with BHV-I genomic DNA. Such a molecule may be derived from any suitable plasmid, cosmid or phage, plasmids being most preferred, and contains the modified homologous or the heterologous DNA sequence, if desired operably linked to a promotor. Said DNA sequence and promotor are introduced into a fragment of genomic BHV-I DNA containing the whole or part of the non-essential section of the BHV-I genome as defined herein, sub-cloned in the recombinant DNA molecule.

These so called insertion-region sequences which flank the heterologous DNA sequence should be of appropriate length, e.g. 50–3000 bp, as to allow in vivo homologous recombination with the viral BHV-I genome to occur.

If desired, a construct can be made which contains two or more different heterologous DNA sequences derived from the same or different pathogens said sequences being flanked by insertion-region sequences of BHV-I defined herein. Such a recombinant DNA molecule can be employed to produce recombinant BHV-I which expresses two or more different antigenic polypeptides to provide a multivalent vaccine.

Thus the present invention also relates to a nucleic acid sequence comprising at least part of the section of the BHV-genome that is located 3' adjacent to the gIV gene and extending to the 3' end of ORF-1.

In a preferred form, a recombinant DNA molecule comprising a heterologous DNA sequence, flanked at its 5'- and/or 3'-terminal site by DNA sequences derived from a section of a BHV-I genome as defined above is used for homologous recombination.

More preferably, a recombinant molecule is used for homologous recombination, that comprises the nucleic acid sequence or the recombinant DNA molecule described above, and additionally comprises at least a 3'-terminal part of a gene coding for a BHV-1 gIV polypeptide and a poly-adenylation signal adjacent to the 3'-terminus of this gene.

In a most preferred form, the above mentioned recombinant molecule comprises not only part of the gIV gene, but the whole gIV gene, including a promotor functionally linked to the gene. This recombinant molecule is, after homologous recombination, capable of fully complementing a gIV-negative BHV-1 mutant.

Susceptible cells, e.g. Madin Darby Bovine Kidney cells (MDBK-cells) or bovine embryo cells can be transfected with BHV-1 DNA in the presence of the recombinant DNA molecule comprising a heterologous DNA sequence, and also comprising a poly-A signal located upstream the heterologous DNA sequence as defined above, flanked at its 5'- and/or 3'-terminal site by DNA sequences derived from a section of the BHV-1 genome as defined in the present invention whereby recombination occurs between the insertion-region sequences in the recombinant DNA molecule and the insertion-region sequences in the BHV-I genome.

Recombination can also be brought about by first transfecting cells with a nucleic acid sequence containing the modified homologous DNA sequence or heterologous DNA sequence flanked by appropriate insertion-region sequences, followed by infection with BHV-I.

Recombinant viral progeny is thereafter produced in cell culture and can be selected for example genotypically or phenotypically, e.g. by hybridization, detecting enzyme activity encoded by a gene co-integrated along with the heterologous DNA sequence or detecting the antigenic heterologous polypeptide expressed by the recombinant BHV-I immunologically. Recombinant virus can also be selected positively based on resistance to compounds such as neomycine, gentamycine or mycophenolic acid. The selected recombinant BHV-I can be cultured on a large scale in cell culture after which BHV-I mutant-containing material or heterologous polypeptides expressed by said BHV-I mutant can be collected thereof.

As mentioned above, the BHV-1 mutant may also have deletions in the ORF-1 coding region. One way of introducing deletions is cloning of the BHV-1 section defined above into a plasmid, selective cutting of the BHV-1 section defined above with suitable restriction-enzymes that cut in ORF-1, removal of the fragment that was cut, and recircularisation of the remaining plasmid molecule.

Recircularization would result in a derivative lacking at least part of the coding sequence present within the newly identified region.

Alternatively, progressive deletions can be introduced either in one or two directions starting from within a restriction site present within the sequence of an open reading frame. Enzymes such as Bal31 or exonuclease III can be used for this purpose. Recircularized plasmid molecules are transformed into E. coli cells and individual colonies are analyzed by restriction mapping in order to determine the size of the deletion introduced into the specified region. An accurate positioning of the deletion can be obtained by sequence analysis. The plasmid containing a defined deletion can be cotransfected with BHV-I viral DNA into cultured bovine cells. After in vivo recombination has occurred, the deletion will be introduced at the correct position within the described region of the viral genome. Recombinants among the viral progeny can be identified for example by means of 15 to 20 bases long synthetic oligomer which hybridizes specifically to the nucleotide sequence which is generated at the junction where the deletion originally was introduced.

A live BHV-I mutant according to the present invention, and in particular a live BHV-I expressing one or more different heterologous polypeptides of specific pathogens, can be used to vaccinate cattle. Vaccination with such a live vector vaccine is preferably followed by replication of the BHV-I mutant within the inoculated host, expressing in vivo the heterologous polypeptide along with the BHV-I polypeptides. The polypeptides expressed in the inoculated host will then elicit an immune response against both BHV-I and the specific pathogen. If the heterologous polypeptide derived from the specific pathogen can stimulate a protective immune response, then the animal inoculated with the BHV-I mutant according to the invention will be immune to subsequent infection by that pathogen as well as to infection by BHV-I. Thus, a heterologous nucleic acid sequence incorporated into the insertion-region of the BHV-I genome according to the invention may be continuously expressed in vivo, providing a solid, safe and long-lasting immunity to a pathogen.

A BHV-I mutant according to the invention containing and expressing one or more different heterologous polypeptides can serve as a monovalent or multivalent vaccine.

For the preparation of a live vaccine the BHV-I mutant according to the present invention can be grown on susceptible cells.

Growth can e.g. be performed on a cell culture of bovine origin.

The viruses thus grown can be harvested by collecting the tissue cell culture fluids and/or cells. The live vaccine may be prepared in the form of a suspension or may be lyophilized.

In addition to an immunogenically effective amount of the recombinant BHV-I the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity-may be added to the vaccine. Suitable adjuvants are for example aluminium hydroxide, phosphate or oxide, oil-emulsions (e.g. of Bayol F® or Marcol52®), saponins or vitamin-E solubilisate.

The useful effective amount to be administered will vary depending on the age, weight, mode of administration and type of pathogen against which vaccination is sought. A suitable dosage can be for example about $10^3$–$10^7$ pfu/animal.

An BHV-I mutant according to the invention can also be used to prepare an inactivated vaccine.

For administration to animals, the BHV-I mutant according to the present invention can be given inter alia intranasally, intradermally, subcutaneously or intramuscularly.

It is a further object of the present invention to produce subunit vaccines, pharmaceutical and diagnostic preparations comprising a heterologous polypeptide expressed by an BHV-I mutant according to the invention. This can be achieved by culturing cells infected with said BHV-I under conditions that promote expression of the heterologous polypeptide. The heterologous polypeptide may then be purified with conventional techniques to a certain extent depending on its intended use and processed further into a preparation with immunizing, therapeutic or diagnostic activity.

The above described active immunization against specific pathogens will be applied as a protective treatment in healthy animals. It goes without saying that animals already infected with a specific pathogen can be treated with antiserum comprising antibodies evoked by a BHV-I mutant according to the invention comprising a heterologous gene derived from the specific pathogen encoding an antigenic polypeptide. Antiserum directed against a recombinant BHV-I according to the invention can be prepared by immunizing animals, for example cattle, with an effective amount of said BHV-I mutant in order to elicit an appropriate immune response. Thereafter the animals are bled and antiserum can be prepared.

Homologous recombination is occurring only at a very low frequency. Therefore, selection of a recombinant BHV-I virus generally is very time-consuming.

The present invention offers a method to avoid selection for homologous recombinants, by using a self-selecting system. In general, the fact that a gene is essential for a virus implicates that no virus can be grown that is deprived of the genetic information to express the functional gene product unless the cell complements for the missing gene product.

This implicates, that it is impossible to grow infectious virus that is genotypically negative for the essential polypeptide gIV, unless this virus is grown on a gIV-complementing cell-line.

In the present invention, it is shown for the first time, how this phenomenon can be used to avoid time-consuming selection procedures as follows: A virus, genotypically negative for an essential gene can only be grown in cells that are continuously complementing the missing gene-product. In that case, infectious virus will emerge, that is capable of infecting non-complementing cells, but is not capable of reproduction. When however the DNA of the virus is transfected into a non-complementing cell together with a recombinant DNA having homologous DNA sequences flanking an intact copy of the gene missing in the virus, this may lead to homologous recombination restoring the essential gene function in the viral genome.

As a result, this virus will be the only virus that, by regaining its essential information, is capable of reproduction on non-complementing cells. Therefore the process is self-selective.

Therefore, in a further form of the invention, a method is used for the construction of a BHV-I mutant comprising bringing together in a suitable host cell a recombinant DNA molecule comprising the genetic information for functional expression of the gIV polypeptide said genetic information being flanked at its 5'- and 3'-terminal site by DNA sequences derived from a section of a BHV-I genome that comprises a gene or an intergenic region, and a genotypically gIV-negative BHV-1 virus or the DNA of such a genotypically gIV-negative BHV-1 virus.

The section of the BHV genome may comprise an essential gene or a non-essential gene. This depends on the aim of the experiment. If the goal is to inactivate an essential gene, flanking sequences could be derived from this essential gene. Recombinant viruses will then lack the functional essential gene. If the goal is, to merely insert foreign sequences, a non-essential gene or a non-essential intergenic region will usually be used to provide the flanking sequences.

In a more preferred form, a method will be used in which the genetic information also comprises a heterologous gene.

Such a heterologous gene may be derived, e.g. a bovine pathogen, e.g. from the group consisting of Bovine Rotavirus, Bovine Viral Diarrhoea virus, Parainfluenza type 3 virus, Bovine Paramyxovirus, Foot and Mouth Disease virus, Bovine Coronavirus, Bovine Respiratory Syncytial virus and Pasteurella haemolytica.

Transfection of the recombinant DNA molecule together with DNA of said virus, that lacks the genetic information to produce a functional gIV polypeptide leads after homologous recombination to a viable virus carrying both the necessary genetic information for gIV and the desired mutation, e.g. the inserted genetic information for a foreign antigen. In a variation on this method, cells are transfected with the recombinant DNA molecule and infected with the virus that lacks the genetic information to produce a functional gIV polypeptide.

In an even more preferred form of the invention, a method is used, that comprises bringing together in a suitable host cell a recombinant DNA molecule that comprises a section of the BHV-1 mutant according to the present invention and at least a 3'-terminal part of the gene coding for gIV and a poly-A signal adjacent to the 3'-terminus of this gene, and a genotypically gIV-negative BHV-I virus from which the 3'-terminal genetic information of the gIV gene present in the recombinant DNA molecule or less is deleted, or the DNA of such a genotypically gIV-negative BHV-1 virus.

In the present invention, preferably a heterologous poly-A signal is chosen as signal 3' adjacent to the gIV gene for the following reason: homologous recombination may occur between:

a) a gIV-negative BHV-1 mutant comprising regions upstream the gIV gene and in or downstream of ORF-1, that are homologous to those in a plasmid, and b) a plasmid comprising one of these homologous regions located upstream of gIV, followed by the gIV gene, a poly-A signal downstream gIV-ORF, a mutation, if necessary a poly-A signal downstream of the mutation, and finally the other homologous region.

If as a poly-A signal 3' terminal of gIV the authentic gIV-poly-A signal is used, it is possible that the typical 3' site at which homologous recombination cross-over occurs, comprises the context of the poly-A signal. In that case, all sequences downstream of the poly-A site would not be transferred to the BHV-1 virus during the recombination event. As a result, the mutation as described in the present invention, e.g. the heterologous gene would not be transferred to the mutant virus.

Insertion of a heterologous poly-A signal 3' adjacent to the gIV gene and insertion of the authentic poly-A signal downstream of the mutation solves this problem: no recombination between heterologous poly-A signals can happen since the poly-A consensus-sequence is statistically too short to allow homologous recombination. Thus, if 3' homologous recombination occurs at the poly-A signal, this can only be the authentic poly-A signal and therefore all genetic information in between this signal and the 5' homologous recombination site is also transferred.

It is not necessary that the whole gIV gene is present on the recombinant DNA molecule if the viral DNA still comprises the part of the gIV gene missing on the recombinant DNA molecule and an overlapping gIV fragment: if an overlapping sequence for homologous recombination is located in the gIV genome, recombination leads to a full-length gene.

The advantage of the method for the production of BHV-1 mutants described above, is that the only viable progeny viruses are viruses that successfully passed homologous recombination.

This avoids the laborious and timeconsuming screening procedures that normally follow homologous recombination experiments.

For homologous recombination, a BHV-I mutant virus is used, that has a mutation in the part of gIV that is incorporated in the recombinant DNA molecule or less than that part, and as a result is not capable of expressing functional gIV polypeptide. This mutant is grown on a gIV complementing cell line as described by Fehler et al. (Fehler et al., J. of Virol., 66: 831–839 (1992)). As a result, only BHV-I viruses that recombined successfully obtained the genetic information for expression of a functional gIV polypeptide. Thus, only these viruses are capable of multiple replication in non-complementing host cells. The method therefore provides an extremely efficient and simple way of screening for successful homologous recombination events.

The usefulness of the method for the highly efficient production of BHV-1 mutants as described above is not limited to the combination of the non-essential region ORF-1 as disclosed in the present application with the gIV gene.

A recombinant DNA molecule comprising the gene coding for gIV, including promotor and poly-adenylation sites, i.e. the genetic information for functional expression of the gIV polypeptide which genetic information is additionally flanked at its 3'- and 5' ends by fragments from any gene or intergenic region of BHV-1 can be used in combination with a gIV-negative BHV-1 virus for homologous recombination. Homologous recombination then leads to complementation of the gIV-gene, albeit not at its native site.

This method may e.g. be used to introduce an insertion in a gene in order to inactivate this gene. Interesting gene candidates for this approach of insertion-inactivation are e.g. genes, involved in virulence.

Preferably, the genetic information mentioned above is extended with additional genetic information. This additional information may be in the form of a heterologous gene.

Although not necessarily, in many cases a gene or intergenic region known to be non-essential in BHV-I will be chosen as the preferred insertion site for gIV.

In a preferred form, a recombinant DNA molecule comprising the gene coding for gIV, including promotor and poly-adenylation sites, and additionally comprising a heterologous gene, which recombinant DNA molecule is additionally flanked at its 3'- and 5' ends by fragments from any gene or intergenic region known to be non-essential in BHV-I is used.

The gI-gene (Whitbeck et al.; J. Virol. 62: 3319–3327 (1988)), the gIII-gene (Fitzpatrick et al.; Virology 173: 46–57 (1989)) or the TK-gene (Kit et al., U.S. Pat. Nos. 4,703,011 and 4,824,667) as mentioned above and all three known to be non-essential genes could for example be used as a possible integration site for a gIV/foreign gene construct, analogous to the principles described above for ORF-1.

EXAMPLE 1

Localisation of the gIV-poly-A signal

Figure 1B:
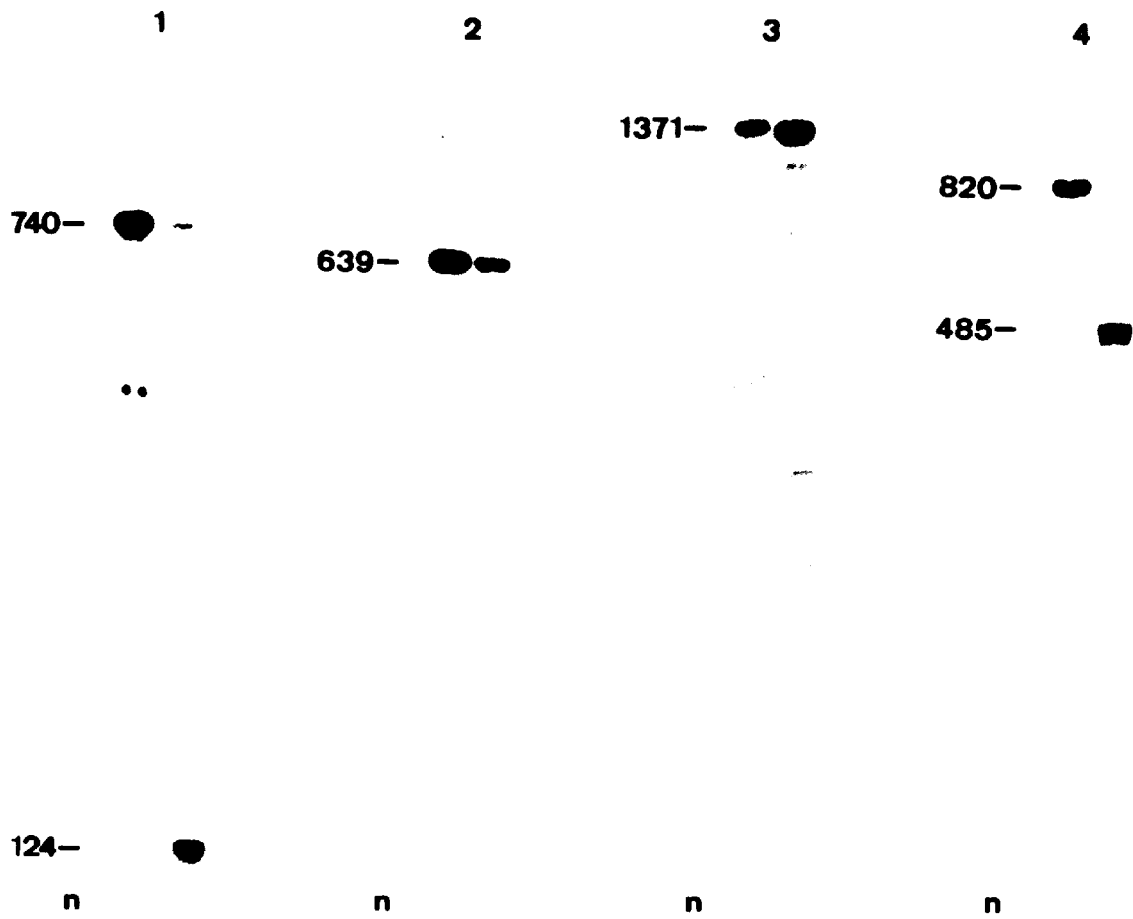
FIG. 1B. Experimental data showing the undigested probe on the left and the protected fragment on the right.

In order to demonstrate that the poly-A signal used by gIV is the same signal used by ORF-1, the following experiment was done: the HindIII L fragment was cleaved with SalI and fragments containing gIV and ORF-1 were labeled with $^{32}$P at the 5'-end (FIG. 1a, closed circle) or 3'-end (FIG. 1a, open circle). Labeled fragments were hybridized to RNA from BHV-1 infected cells and, after nuclease S1 digestion, separated on denaturing acrylamide gels. Labeled fragments were visualized by autoradiography. The size of the protected fragments was determined using sequencing reactions and end-labeled DNA markers; sizes of the probes were determined from the sequence. The results show, that the infected cell RNA protects 124 nucleotides (n) of the 740 n 5'-end labeled fragment (A in FIG. 1a, lane 1 in FIG. 1b), the full lengths of the 3'-labeled 639 n and 1371 n fragments (FIG. 1b, lanes 2 and 3) and 485 n of the 3'-labeled 820 n fragment (FIG. 1b, lane 4). This demonstrates that the 5'-end of the gIV mRNA is 124 n upstream of the rightward SalI cleavage site (25 n downstream the TATA-box, and 485 n downstream the leftward SalI cleavage site (45 n downstream the poly-A signal). No RNA discontinuity was found in between. Thus the transcript coding for gIV spans 2655 nucleotides of the genomic sequence (C) and contains both the gIV-ORF and ORF-1.

EXAMPLE 2

Figure 3:
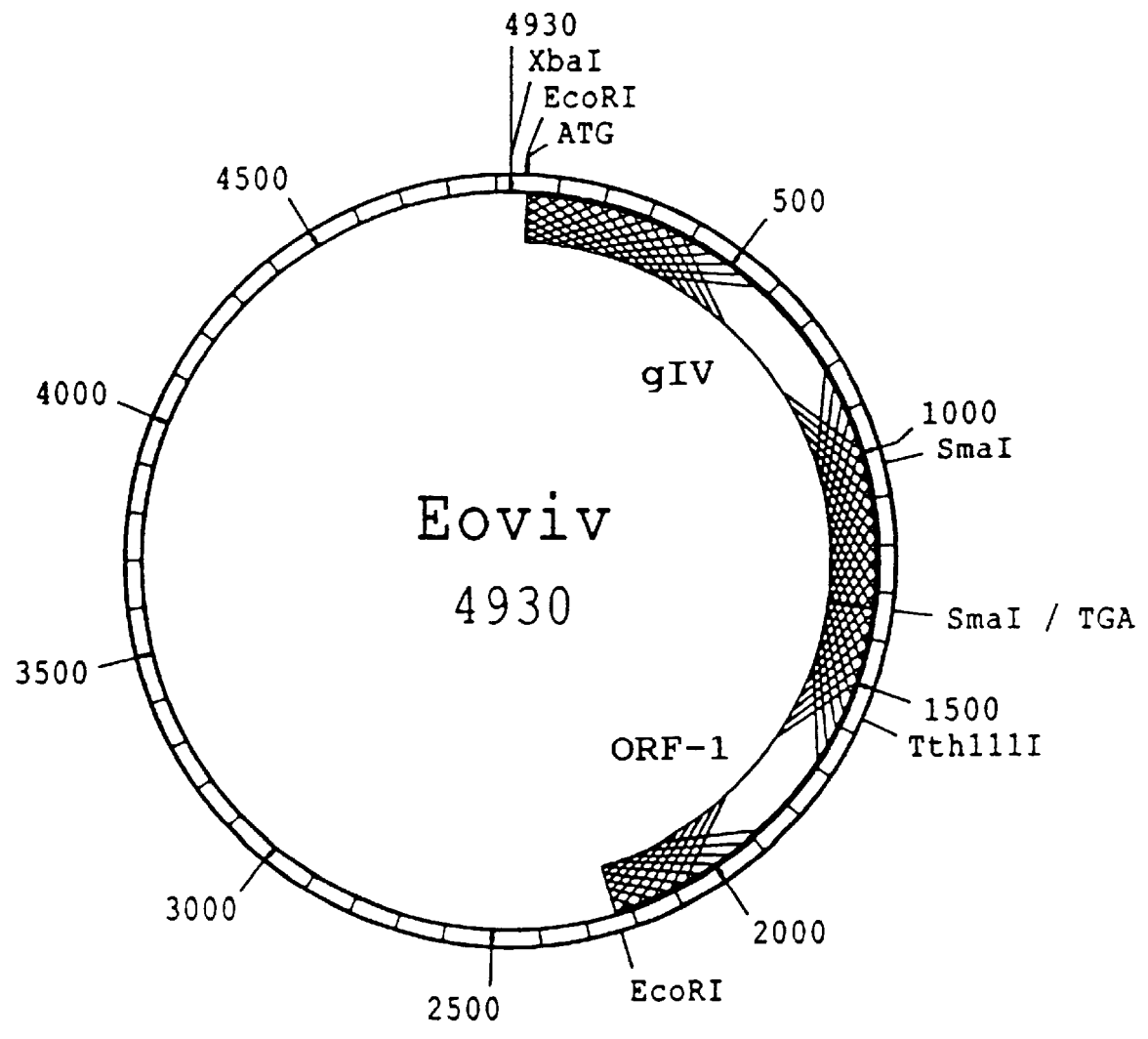
Figure 4:
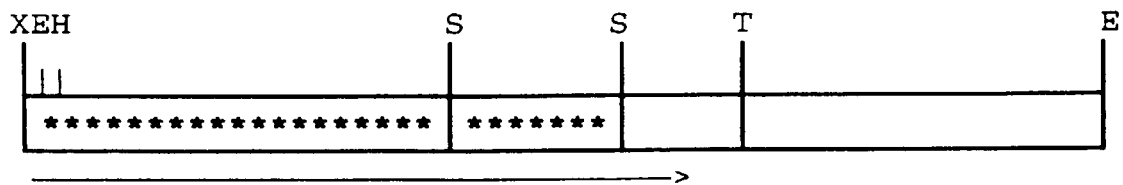
FIG. 4. Construction of pEMBL19-gIV-ORF.
Figure 4:
Figure 4:
Figure 4:
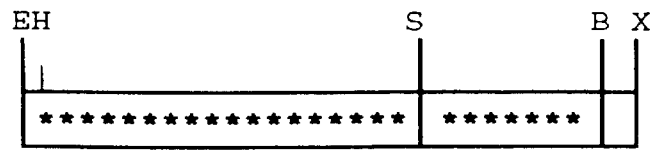

Construction of a plasmid carrying the gIV gene including promotor and termination signals The first step in constructing this plasmid was the isolation of the gIV ORF from the plasmid Eoviv (FIG. 3). This plasmid contains a 2,2 kbp fragment carrying the gIV-ORF and ORF-1. It was incubated with Tth111I, which cleaves within ORF-1 (see FIG. 4). To remove ORF-1 specific sequences the cleaved DNA was incubated with exonuclease Bal31 followed by cleavage with XbaI, which cuts upstream the translational start codon for gIV, and recessive ends were filled with the Klenow fragment of E. coli DNA-polymerase I (Klenow-polymerase). The reaction products were size separated in agarose gels and DNA fragments of the expected size were isolated and integrated into the plasmid vector pEMBL19®, linearized with SmaI. DNA of resulting clones was sequenced to determine the extend of the ORF-1 specific sequence deletion. One clone, lacking the entire ORF-1 and 12 nucleotides of the 3'-end of the gIV ORF was cleaved with EcoRI and religated. This step was necessary because due to the cloning procedure this plasmid contained several restriction enzyme cleavage sites 5' to the gIV-ORF flanked by EcoRI cleavage sites. The resulting plasmid was named pEMBL19-gIV-ORF (see FIG. 4).

Figure 5:
FIG. 5. Construction of gIV-ORF/pLA1-6.
Figure 5:
Figure 5:
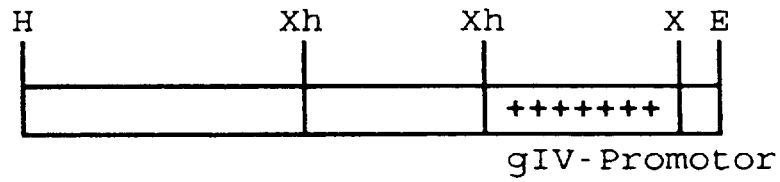

To provide the gIV-ORF with the authentic gIV promoter and with additional sequences upstream the gIV gene for the foreseen integration into the BHV-1 genome, pEMBL19-gIV DNA was cleaved with HindIII (upstream the ORF) and XbaI at the truncated 3' end of the gIV-ORF and recessive ends were filled in with Klenow-polymerase (see FIG. 5). The DNA fragment was integrated into plasmid pLA1-6, cleaved with BamHI and EcoRI and blunt-ended with Klenow-polymerase. Plasmid pLA1-6 contains the gIV promoter followed by a polylinker sequence and sequences upstream of the gIV gene. The plasmid with the correct orientation of the (still 3' truncated) gIV-ORF was named pLA1-6-gIV. To complete the gIV-ORF and to add a molecular biological marker a synthetic oligonucleotide was inserted into the BamHI cleavage site adjacent to the truncated gIV-ORF. The resulting plasmid that now contained the complete gIV-ORF was named pLA1-6-gIV-ORF (see FIG. 6).

Figure 8:
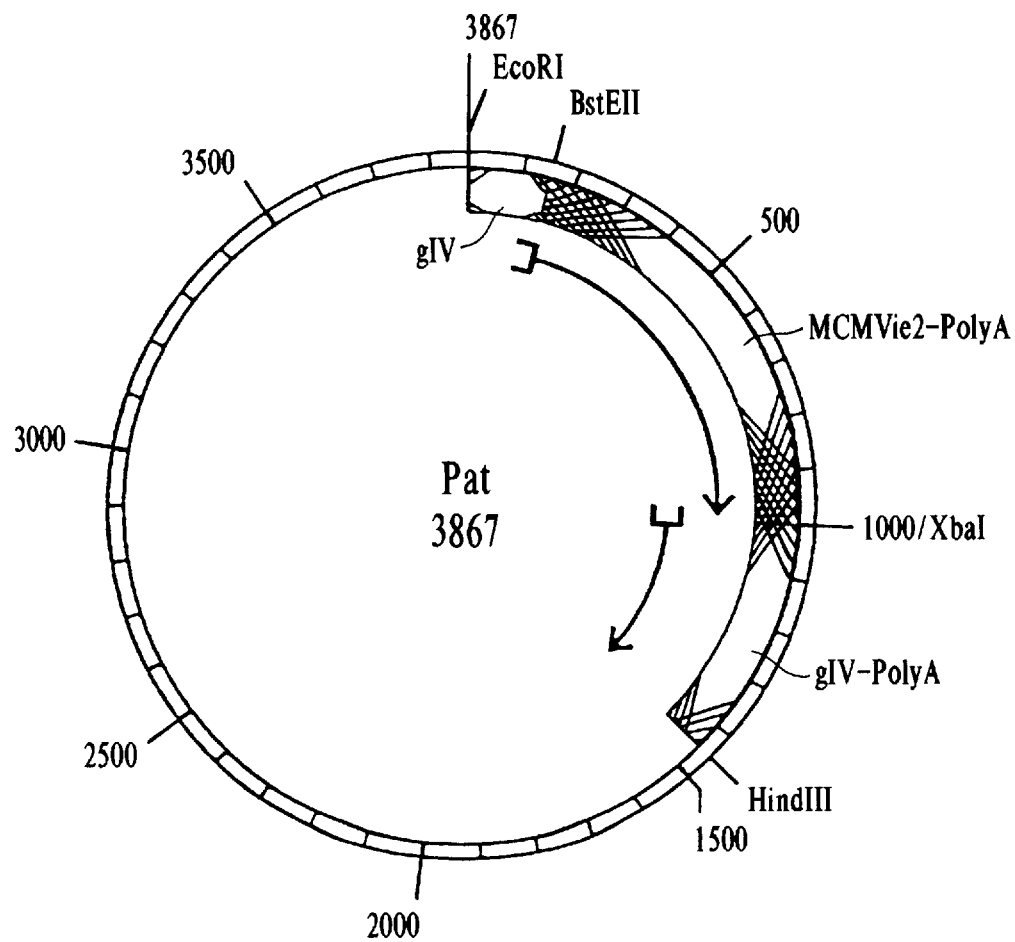
FIG. 8. Physical map of Pat 3867.
Figure 9:
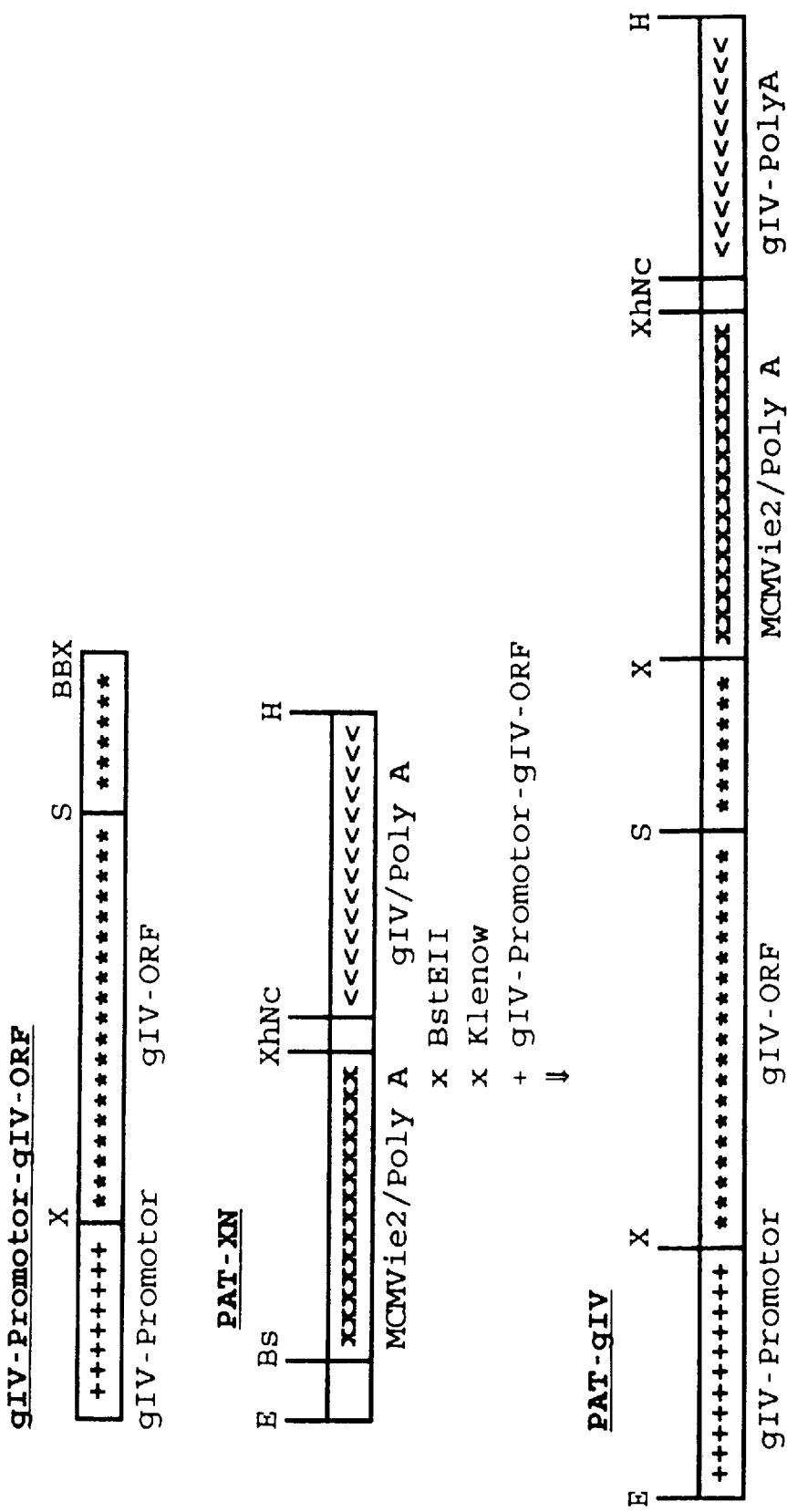
FIG. 9. Construction of pAT-gIV.

To construct a complete gIV-gene and a recombination plasmid suitable for the deletion of ORF-1 out to the BHV-1 genome, plasmid DNA of pLA1-6-gIV-ORF was cleaved with XhoI and EcoRI, blunt-ended with Klenow-polymerase and a DNA fragment containing upstream gIV sequences, gIV-promoter and the restored gIV-ORF (see FIG. 7) was inserted into plasmid pAT-XN treated with BstEII and Klenow-polymerase. Plasmid pAT-XN is based on Pat 3867 that contains the poly-adenylation signal of the murine cytomegalovirus (MCMV) immediate early 2 (ie2) gene (Messerle et al.; J. Virol 65: 1638 ff. (1991)) adjacent to the BstEII site (see FIG. 8). The MCMV sequences are followed by cleavage sites for XhoI and NcoI and downstream gIV sequences required for homologous recombination into the BHV-1 genome. This was accomplished by inserting the oligonucleotide sequence CTCGAGCCATGG into the XbaI site in Pat 3867. The resulting plasmid was named pAT-gIV and used for the deletion of ORF-1 (see FIG. 9).

To further demonstrate that the addition of a heterologous polyadenylation signal enables also the integration of additional genes in this region of the BHV-1 genome, plasmid DNA of pAT-gIV was cleaved with NcoI and blunt ended with Klenow-polymerase. The ORF for the bacterial enzyme chloramphenicol acetyltransferase under control of the MCMV early 1 (e1) promoter (Bühler et al.; J. Virol. 64: 1907 ff. (1990)) was integrated into the linearized pAT-gIV DNA, giving the plasmid pAT-gIV CAT.

EXAMPLE 3

Deletion of ORF-1 from the BHV-1 genome MDBK cells were transfected with 5 µg DNA of pAT-gIV 24 h after seeding using the calcium phosphate precipitation technique. Transfected cells were shocked with glycerol 4 h after addition of the DNA and cultures were infected with phenotypically complemented gIV- virus BHV-1/80–221 (Fehler et al., J. of Virol., 66: 831–839 (1992)) with a multiplicity of 10 PFU per cell. 48 h p.i. the cells were harvested and the cell culture supernatant was used for the infection of MDBK cells. Under these conditions only genotypically gIV positive virions can grow productively and form plaques on the monolayers. 3 days p.i. virions from single plaques were isolated and DNA from MDBK cells was purified, cleaved with HindIII, size separated by agarose gel electrophoresis and transferred to nitrocellulose filters. Filters were hybridized with $^{32}$P-labeled DNA either from the MCMV-ie2 polyadenylation signal, the β-galactosidase-ORF, ORF-1 or the sequences downstream ORF-1 presented for homologous recombination. The results demonstrate that the isolated virions lack the β-galactosidase sequences, that ORF-1 is deleted and that the gIV-ORF and the MCMV-ie2 DNA is integrated. From the size of the hybridizing fragments it is concluded that the integration of pAT-gIV Sequences occurred via homologous recombination. Isolated virions were plaque purified twice to ascertain homologous preparations. The ORF-1$^-$ virus was designated BHV-1-ORF-1$^{31}$. The determination of the viral growth characteristics (release and total yield from infected cell cultures) and the adsorption and penetration behaviour of the mutant in comparison to wild type virus showed that the deletion of ORF-1 did not affect these parameters in cell culture.

Deletion of ORF-1 and integration of the CAT gene

MDBK cells were transfected with 5 μg DNA of pAT-gIVCAT 24 h after seeding using the calcium phosphate precipitation technique. Transfected cells were shocked with glycerol 4 h after addition of the DNA and cultures were infected with phenotypically complemented gIV virus BHV-1/80–221 with a multiplicity of 10 PFU per cell. 48 h p.i. the cells were harvested and the cell culture supernatant was used for the infection of MDBK cells. Under these conditions only genotypically gIV positive virions can grow productively and form plaques on the monolayers. 3 days p.i. virions from single plaques were isolated and DNA from MDBK cells was purified, cleaved with HindIII, size separated by agarose gel electrophoresis and transferred to nitrocellulose filters. Filters were hybridized with $^{32}$P-labeled DNA either from the CAT-ORF, the β-galactosidase-ORF, ORF-1 or the sequences downstream ORF-1 presented for homologous recombination. The results demonstrate that the isolated virions lack the β-galactosidase sequences, that ORF-1 is deleted and that the gIV-ORF and the MCMVe1-CAT DNA are integrated. From the size of the hybridizing fragments it is concluded that the integration of pAT-gIV sequences occurred via homologous recombination. Isolated virions were plaque purified twice to ascertain homologous preparations. The ORF-1$^{31}$/CAT$^+$virus was designated BHV-1CAT. The determination of the viral growth characteristics (release and total yield from infected cell cultures) and the adsorption and penetration behaviour of the mutant in comparison to wild type virus showed that the replacement of ORF-1 by the CAT gene did not affect these parameters in cell culture.

Figure 10:
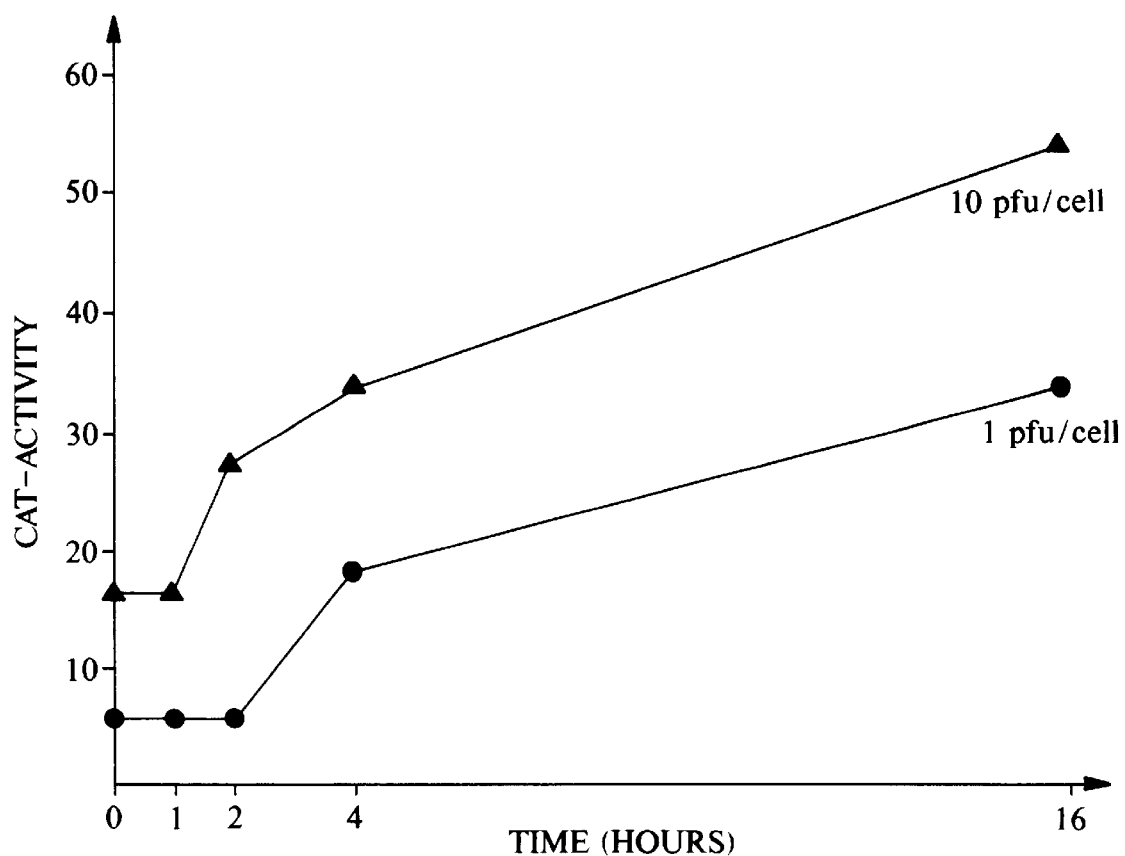
FIG. 10. Correlation between CAT-activity and multiplicity of infection, and increase of CAT-activity in time.

Additionally, as can be seen from FIG. 10, expression of the CAT-gene is also unaffected as shown by the production of CAT and the raise in CAT activity after increasing time.

There is also a clear correlation between the number of viruses (=plaqueforming units) and CAT production level.

In conclusion: replacement of the ORF-1 gene by the CAT gene does not interfere with absorbtion and penetration behaviour of the virus, and the CAT gene is actively expressed is its new context.

I claim:

1. A BHV-1 mutant comprising an insertion of a heterologous DNA sequence in a section of a BHV-1 genome located in the region beginning with the 3' terminus of gIV and extending to the 3'-terminus of ORF-1, wherein ORF-1 codes for a polypeptide that has the amino acid sequence shown in SEQ ID NO:2, and additionally comprising an inserted polyadenylation signal, which is located after the 3' terminus of the gIV gene and before the 5' terminus of the insertion.

2. The BHV-1 mutant according to claim 1, wherein said section of the BHV-1 genome has the DNA sequence shown in SEQ ID NO:1.

3. The BHV-1 mutant according to claim 1, wherein the heterologous DNA sequence encodes a polypeptide.

4. The BHV-I mutant according to claim 3, wherein the heterologous DNA sequence encoding a polypeptide is under the control of a promoter regulating the expression of said heterologous DNA sequence in a cell infected with said BHV-I mutant.

5. The BHV-I mutant according to claim 3, wherein said heterologous DNA sequence encodes an antigen of a bovine pathogen.

6. The BHV-I mutant according to claim 5, wherein the pathogen is selected from the group consisting of Bovine Rotavirus, Bovine Viral Diarrhoea virus, Parainfluenza type 3 virus, Bovine Paramyxovirus, Foot and Mouth Disease virus, Bovine Coronavirus, Bovine Respiratory Syncytial virus and Pasteurella haemolytica.

7. The BHV-I mutant according to claim 3, wherein the heterologous DNA sequence encodes a cytokine.

8. The BHV-I mutant according to claim 1, wherein at least part of the DNA sequence of said section of the BHV-I genome is deleted.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1289 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Bovine herpesvirus ( i x ) FEATURE:
        ( A ) NAME/KEY: CDS
        ( B ) LOCATION: 142..1095
        ( D ) OTHER INFORMATION: /product="Protein"
            / standard_name= "ORF-1"

( i x ) FEATURE:
        ( A ) NAME/KEY: misc_RNA
        ( B ) LOCATION: 1..3
        ( D ) OTHER INFORMATION: /function="stop-codon gIV"

( i x ) FEATURE:
        ( A ) NAME/KEY: misc_RNA
        ( B ) LOCATION: 4..141
        ( D ) OTHER INFORMATION: /function="untranslated
            region"

( x i ) SEQUENCE DESCRIPTION: SEQ ID NO: 1:

```
TGAGCGGCCT   AGGCCCTCCC   CCGACCGCCC   CCTTTGCTCC   TAGCCCCCGG   CTCCAGCCGA          60

GCCGCGCGGG   GCGGGAGATA   AAGCGCCCGC   GCGGCGGCGA   CTCAGGCCAT   TGCCGCGACC         120

TTGTCCTCCG   GCGCGCTCGC  G  ATG  CGG  CGC  CTG  TTG  CTC  TGG  ATG  GTG  GTG         171
                           Met  Arg  Arg  Leu  Leu  Leu  Trp  Met  Val  Val
                            1                    5                         10

CTG  GCC  GCG  CGA  GCG  GCG  CCC  GCT  CGC  AGC  CTT  GTG  TAT  CGC  GGC  GAG      219
Leu  Ala  Ala  Arg  Ala  Ala  Pro  Ala  Arg  Ser  Leu  Val  Tyr  Arg  Gly  Glu
               15                         20                         25

GCA  GTC  GGC  CTG  CGC  GCG  GAC  GGC  CCC  GTA  GCG  TTC  GCT  GTC  CAC  CCG      267
Ala  Val  Gly  Leu  Arg  Ala  Asp  Gly  Pro  Val  Ala  Phe  Ala  Val  His  Pro
                    30                         35                    40

ACC  GAC  GCA  ACG  CTC  GCG  CTG  CGG  GGC  CGG  CTG  ATT  TTC  CTA  GAA  CAC      315
Thr  Asp  Ala  Thr  Leu  Ala  Leu  Arg  Gly  Arg  Leu  Ile  Phe  Leu  Glu  His
               45                         50                    55

CAG  CTC  CCG  GCC  GGG  CGG  CGC  TAC  AAC  GGG  ACC  GTC  GAG  CTG  CTG  CGC      363
Gln  Leu  Pro  Ala  Gly  Arg  Arg  Tyr  Asn  Gly  Thr  Val  Glu  Leu  Leu  Arg
          60                         65                    70

TAC  CAC  GCC  GCG  GGC  GAC  TGC  TTC  GTT  ATG  CTG  CAG  ACG  ACC  GCG  TTC      411
Tyr  His  Ala  Ala  Gly  Asp  Cys  Phe  Val  Met  Leu  Gln  Thr  Thr  Ala  Phe
75                         80                         85                    90
```

| | | | | | | | | | | | | | | | | |
|---|---|---|---|---|---|---|---|---|---|---|---|---|---|---|---|---|
| GCC | TCC | TGC | CCG | CGC | GTC | GCG | AAC | GAC | GCC | TTT | CGC | TCC | TGC | CTG | CAC | 459 |
| Ala | Ser | Cys | Pro | Arg | Val | Ala | Asn | Asp | Ala | Phe | Arg | Ser | Cys | Leu | His | |
| | | | | 95 | | | | | 100 | | | | | 105 | | |
| GCC | GAC | ACG | CGC | CCC | GCT | CGC | AGC | GAG | CGG | CGC | GCG | AGC | GCC | GCG | GTC | 507 |
| Ala | Asp | Thr | Arg | Pro | Ala | Arg | Ser | Glu | Arg | Arg | Ala | Ser | Ala | Ala | Val | |
| | | | 110 | | | | | 115 | | | | | 120 | | | |
| GAA | AAC | CAC | GTG | CTC | TTC | TCC | ATC | GCC | CGT | CCG | CGC | CCA | ATA | GAC | TCG | 555 |
| Glu | Asn | His | Val | Leu | Phe | Ser | Ile | Ala | Arg | Pro | Arg | Pro | Ile | Asp | Ser | |
| | | 125 | | | | | 130 | | | | | 135 | | | | |
| GGG | CTC | TAC | TTT | CTG | CGC | GTC | GGC | ATC | TAC | GGC | GGC | ACC | GCG | GGC | AGC | 603 |
| Gly | Leu | Tyr | Phe | Leu | Arg | Val | Gly | Ile | Tyr | Gly | Gly | Thr | Ala | Gly | Ser | |
| | 140 | | | | | 145 | | | | | 150 | | | | | |
| GAG | CGC | CGC | CGA | GAC | GTC | TTT | CCC | TTG | GCC | GCG | TTT | GTA | CAC | AGC | TTC | 651 |
| Glu | Arg | Arg | Arg | Asp | Val | Phe | Pro | Leu | Ala | Ala | Phe | Val | His | Ser | Phe | |
| 155 | | | | | 160 | | | | | 165 | | | | | 170 | |
| GGT | GAG | CCC | GGA | GAC | CCA | GAG | GCC | GCG | GCC | GCG | CAC | CCC | GGC | ACC | GTC | 699 |
| Gly | Glu | Pro | Gly | Asp | Pro | Glu | Ala | Ala | Ala | Ala | His | Pro | Gly | Thr | Val | |
| | | | | 175 | | | | | 180 | | | | | 185 | | |
| GAG | GCA | GTC | GAG | GCC | CGC | TGC | GAG | CGG | GGC | CTC | GAC | GCC | AGC | TCG | GCG | 747 |
| Glu | Ala | Val | Glu | Ala | Arg | Cys | Glu | Arg | Gly | Leu | Asp | Ala | Ser | Ser | Ala | |
| | | | 190 | | | | | 195 | | | | | 200 | | | |
| AGC | CTC | TAC | GAC | CGC | GCG | CTG | GCG | GCG | TTC | CCC | GCA | GGC | GCC | GCC | ACC | 795 |
| Ser | Leu | Tyr | Asp | Arg | Ala | Leu | Ala | Ala | Phe | Pro | Ala | Gly | Ala | Ala | Thr | |
| | | 205 | | | | | 210 | | | | | 215 | | | | |
| ACG | CCC | GGC | CCC | ACC | GCG | AGC | AGC | GAG | AGC | GGG | GCC | GCG | ACG | CCA | GAG | 843 |
| Thr | Pro | Gly | Pro | Thr | Ala | Ser | Ser | Glu | Ser | Gly | Ala | Ala | Thr | Pro | Glu | |
| | 220 | | | | | 225 | | | | | 230 | | | | | |
| AGG | GTC | GAC | GAG | ACG | ACG | GAA | GTC | GAG | GCC | GCG | ACG | AGA | GCG | GGC | TCG | 891 |
| Arg | Val | Asp | Glu | Thr | Thr | Glu | Val | Glu | Ala | Ala | Thr | Arg | Ala | Gly | Ser | |
| 235 | | | | | 240 | | | | | 245 | | | | | 250 | |
| GCG | TTT | GCC | CTC | ACC | ACG | CCC | CCG | GCC | GGC | CCG | ACC | GCC | AGC | CCC | GCC | 939 |
| Ala | Phe | Ala | Leu | Thr | Thr | Pro | Pro | Ala | Gly | Pro | Thr | Ala | Ser | Pro | Ala | |
| | | | | 255 | | | | | 260 | | | | | 265 | | |
| GCC | AGC | CCC | TCC | CGT | GCC | TTT | AGC | GCG | GCC | GCC | CCG | GCC | GCC | GCT | GCG | 987 |
| Ala | Ser | Pro | Ser | Arg | Ala | Phe | Ser | Ala | Ala | Ala | Pro | Ala | Ala | Ala | Ala | |
| | | | 270 | | | | | 275 | | | | | 280 | | | |
| CAG | CCG | GCC | GGA | GAC | ACG | CCC | GCT | CGC | TTC | CGG | CGC | CAA | CTG | GCG | TCG | 1035 |
| Gln | Pro | Ala | Gly | Asp | Thr | Pro | Ala | Arg | Phe | Arg | Arg | Gln | Leu | Ala | Ser | |
| | | 285 | | | | | 290 | | | | | 295 | | | | |
| ATC | CTA | GTG | CCT | CTG | TGC | GTG | CTG | GTG | CTG | CTG | CTG | CTG | CGC | TCT | GCG | 1083 |
| Ile | Leu | Val | Pro | Leu | Cys | Val | Leu | Val | Leu | Leu | Leu | Leu | Arg | Ser | Ala | |
| | | 300 | | | | | 305 | | | | | 310 | | | | |
| CCG | CGA | CGG | TAAACTGCGC | GCTGCGCCGT | CGCCTGCTGC | CGTGCTCTCG | | | | | | | | | | 1132 |
| Pro | Arg | Arg | | | | | | | | | | | | | | |
| 315 | | | | | | | | | | | | | | | | |

| | | | | |
|---|---|---|---|---|
| GCGCGTTTAC | AAGCCGCGGA | CGTGCGCGGC | GTGCGGGAGC | GGCACTGCGC GGGGCGGCCC 1192 |
| CCTGCCGCGG | CGCGGCACCG | AGCGCCCCAG | CCACCGTCGT | GGCACTGGGC TCCCGGCCAA 1252 |
| GGCGCCCCCC | CTCGCCACCA | TCAGCGAAGA | ATAAATT | 1289 |

( 2 ) INFORMATION FOR SEQ ID NO: 2:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | | |
|---|---|---|---|---|---|---|---|---|---|---|---|---|---|---|---|
| Met | Arg | Arg | Leu | Leu | Leu | Trp | Met | Val | Val | Leu | Ala | Ala | Arg | Ala | Ala |
| 1 | | | | 5 | | | | | 10 | | | | | 15 | |

-continued

| | | | | | | | | | | | | | | | |
|---|---|---|---|---|---|---|---|---|---|---|---|---|---|---|---|
| Pro | Ala | Arg | Ser | Leu | Val | Tyr | Arg | Gly | Glu | Ala | Val | Gly | Leu | Arg | Ala |
| | | | 20 | | | | | 25 | | | | | 30 | | |
| Asp | Gly | Pro | Val | Ala | Phe | Ala | Val | His | Pro | Thr | Asp | Ala | Thr | Leu | Ala |
| | | 35 | | | | | 40 | | | | | 45 | | | |
| Leu | Arg | Gly | Arg | Leu | Ile | Phe | Leu | Glu | His | Gln | Leu | Pro | Ala | Gly | Arg |
| | 50 | | | | | 55 | | | | | 60 | | | | |
| Arg | Tyr | Asn | Gly | Thr | Val | Glu | Leu | Leu | Arg | Tyr | His | Ala | Ala | Gly | Asp |
| 65 | | | | | 70 | | | | | 75 | | | | | 80 |
| Cys | Phe | Val | Met | Leu | Gln | Thr | Thr | Ala | Phe | Ala | Ser | Cys | Pro | Arg | Val |
| | | | | 85 | | | | | 90 | | | | | 95 | |
| Ala | Asn | Asp | Ala | Phe | Arg | Ser | Cys | Leu | His | Ala | Asp | Thr | Arg | Pro | Ala |
| | | | 100 | | | | | 105 | | | | | 110 | | |
| Arg | Ser | Glu | Arg | Arg | Ala | Ser | Ala | Ala | Val | Glu | Asn | His | Val | Leu | Phe |
| | | 115 | | | | | 120 | | | | | 125 | | | |
| Ser | Ile | Ala | Arg | Pro | Arg | Pro | Ile | Asp | Ser | Gly | Leu | Tyr | Phe | Leu | Arg |
| | 130 | | | | | 135 | | | | | 140 | | | | |
| Val | Gly | Ile | Tyr | Gly | Gly | Thr | Ala | Gly | Ser | Glu | Arg | Arg | Arg | Asp | Val |
| 145 | | | | | 150 | | | | | 155 | | | | | 160 |
| Phe | Pro | Leu | Ala | Ala | Phe | Val | His | Ser | Phe | Gly | Glu | Pro | Gly | Asp | Pro |
| | | | | 165 | | | | | 170 | | | | | 175 | |
| Glu | Ala | Ala | Ala | Ala | His | Pro | Gly | Thr | Val | Glu | Ala | Val | Glu | Ala | Arg |
| | | | 180 | | | | | 185 | | | | | 190 | | |
| Cys | Glu | Arg | Gly | Leu | Asp | Ala | Ser | Ser | Ala | Ser | Leu | Tyr | Asp | Arg | Ala |
| | | 195 | | | | | 200 | | | | | 205 | | | |
| Leu | Ala | Ala | Phe | Pro | Ala | Gly | Ala | Ala | Thr | Thr | Pro | Gly | Pro | Thr | Ala |
| | 210 | | | | | 215 | | | | | 220 | | | | |
| Ser | Ser | Glu | Ser | Gly | Ala | Ala | Thr | Pro | Glu | Arg | Val | Asp | Glu | Thr | Thr |
| 225 | | | | | 230 | | | | | 235 | | | | | 240 |
| Glu | Val | Glu | Ala | Ala | Thr | Arg | Ala | Gly | Ser | Ala | Phe | Ala | Leu | Thr | Thr |
| | | | | 245 | | | | | 250 | | | | | 255 | |
| Pro | Pro | Ala | Gly | Pro | Thr | Ala | Ser | Pro | Ala | Ala | Ser | Pro | Ser | Arg | Ala |
| | | | 260 | | | | | 265 | | | | | 270 | | |
| Phe | Ser | Ala | Ala | Ala | Pro | Ala | Ala | Ala | Gln | Pro | Ala | Gly | Asp | Thr | |
| | | 275 | | | | | 280 | | | | | 285 | | | |
| Pro | Ala | Arg | Phe | Arg | Arg | Gln | Leu | Ala | Ser | Ile | Leu | Val | Pro | Leu | Cys |
| | 290 | | | | | 295 | | | | | 300 | | | | |
| Val | Leu | Val | Leu | Leu | Leu | Leu | Arg | Ser | Ala | Pro | Arg | Arg | | | |
| 305 | | | | | 310 | | | | | 315 | | | | | |